US008669316B2

(12) United States Patent
Lee et al.

(10) Patent No.: US 8,669,316 B2
(45) Date of Patent: Mar. 11, 2014

(54) MAGNETIC ION-EXCHANGE RESIN AND METHOD FOR THE PREPARATION THEREOF

(75) Inventors: Wen-Chien Lee, Chiayi County (TW); Yu-Zong Lin, Chiayi County (TW); Yu-Sheng Lin, Chiayi County (TW); Tzu-Hsien Wang, Chiayi County (TW)

(73) Assignee: National Chung Cheng University, Chiayi County (TW)

( * ) Notice: Subject to any disclaimer, the term of this patent is extended or adjusted under 35 U.S.C. 154(b) by 15 days.

(21) Appl. No.: 13/482,356

(22) Filed: May 29, 2012

(65) Prior Publication Data

US 2013/0149772 A1 Jun. 13, 2013

(30) Foreign Application Priority Data

Dec. 7, 2011 (TW) .............................. 100145105 A

(51) Int. Cl.
| | | |
|---|---|---|
| *C12N 1/20* | (2006.01) | |
| *H01F 1/00* | (2006.01) | |
| *H01F 1/26* | (2006.01) | |
| *C07H 21/00* | (2006.01) | |
| *C07H 21/04* | (2006.01) | |
| *C08K 3/22* | (2006.01) | |

(52) U.S. Cl.
USPC ............. 524/431; 435/252.33; 252/62.54; 536/25.4; 977/896

(58) Field of Classification Search
USPC ................. 524/431; 526/90; 435/252.33; 252/62.54; 536/25.4; 977/896
See application file for complete search history.

(56) References Cited

U.S. PATENT DOCUMENTS

| | | |
|---|---|---|
| 5,595,666 A | 1/1997 | Kochen et al. |
| 5,652,190 A | 7/1997 | Kochen et al. |
| 5,855,790 A | 1/1999 | Bradbury et al. |
| 6,718,742 B1 | 4/2004 | Baker |
| 7,754,278 B2 * | 7/2010 | Lee et al. ............... 427/129 |

FOREIGN PATENT DOCUMENTS

| | | |
|---|---|---|
| CN | 1680469 | 10/2005 |
| CN | 1699447 | 11/2005 |
| JP | 2001272395 | 10/2001 |
| KR | 20040091385 | 10/2004 |
| TW | 200302233 | 8/2003 |
| TW | 200600194 | 1/2006 |
| TW | I277632 | 4/2007 |
| WO | 2006059655 | 6/2006 |

OTHER PUBLICATIONS

Lee et al. Preparation of Magnetic Ion-Exchange Resins by the Suspension Polymerization of Styrene with Magnetite. Journal of Applied Polymer Science, vol. 89 No. 8 (Jun. 10, 2003) pp. 2058-2067.*
Y. Lee, J. Rho, and B. Jung; "Preparation of Magnetic Ion-Exchange Resins by the Suspension Polymerization of Styrene with Magnetite", J. Appl. Polym. Sci., vol. 89, 2058-2067, (2003).*
Hickstein and Peuker, Biotechnol. Prog., vol. 24, No. 2, 409-416, 2008.
Kappler et al., J. Biosci. Bioeng., vol. 105, No. 6, 579-585, 2008.
6th Conference on Biochemical Engineering, Tatung University, "O-III-4 Preparation Magnetic Ion-Exchange Microspheres for DNA Isolation and Enzyme Immobilization", published on Jun. 24-25, 2011.

* cited by examiner

*Primary Examiner* — Bijan Ahvazi
*Assistant Examiner* — Ronald Grinsted
(74) *Attorney, Agent, or Firm* — WPAT, P.C.; Anthony King; Kay Yang

(57) ABSTRACT

Magnetic ion-exchange polymer microspheres and a method for preparing the same are provided. The method for preparing the magnetic ion-exchange polymer microspheres includes swelling the ion-exchange resins and allowing the magnetic nano-particles to enter the interior of the ion-exchange resins. The magnetic ion-exchange resins of the present invention have various functional groups can be introduced onto the surfaces thereof. Therefore, the magnetic ion-exchange resins of the present invention can be applied in many areas, and thereby they have high economic value.

13 Claims, 5 Drawing Sheets

MAGNETIC ION-EXCHANGE RESIN AND METHOD FOR THE PREPARATION THEREOF

BACKGROUND OF THE INVENTION

1. Field of the Invention

The invention relates to a magnetic ion-exchange resin and a method for the preparation thereof, and more particularly, to a magnetic ion-exchange resin which comprises magnetic particles entrapped within the swelled ion-exchange polymer microspheres and the method for the preparation thereof.

2. The Prior Arts

The magnetic particles can control the motion of particles by external magnetic field, thereby separating and collecting biological molecules, such as cells, DNA, RNA, antibodies, antigens, proteins, and nucleic acid, which can be adsorbed onto the magnetic particles by chemical bonding or physical adsorbing and then are separating from solution. The above process can effectively separate trace amount of target material from mixture by the control of the external magnetic field, without the complicate separating processes such as filter, chromatography, centrifugation, and therefore can be widely used in the biological detection field. In addition, the magnetic particles can be used as the catalysts of biochemical reactions for capturing proteins by chemical bonding or physical adsorption and immobilizing enzyme.

Generally, the ion-exchanging resin is meant to a material with surface charge particles that can combine positive or negative ionic functional groups with resin (usually organic polymer). Ion-exchange resins have ion-exchange capabilities; it can exchange itself with the same electrical ion in the solution. According to different property of ion-exchange groups, the ion-exchange resins can be divided into cation-exchange resin and anion-exchange resin. The cation-exchange resin is known as the resin with negatively charged functional groups such as sulfonic acid on the surface thereof, and the anion-exchange resin is known as the resin with positively charged functional groups such as four amine ions. The cation-exchange resin adopts cations such as sodium ions, or hydrogen ions, and the ion-exchange principle thereof is that cations can be exchanged from the cation-exchange resin if the solution has the same cations of higher concentration or the other cations of stronger adsorption. Therefore, cations can be desorbed from the cation-exchange resin by addition of high concentration of salts (e.g. NaCl). The ion-exchange principle of anion-exchange resin is the same as that of cation-exchange resin, only with the opposite ionic charge.

The magnetic ion-exchange resin is known as combination of magnetic and ion-exchange polymer microspheres. The known manufacturing method for magnetic ion-exchange resin as disclosed in Taiwan Patent Application No. 092100312 includes the steps of: producing a dispersion having a continuous aqueous phase and a dispersed organic phase with one or more polymerizable monomers, magnetic particles and a dispersing agent, polymerizing one or more polymerizable monomers to form polymeric beads incorporating the magnetic particles. The polymeric beads include amine groups capable of complexing a transition metal cation, or the polymeric beads are reacted with one or more compounds to provide amine groups capable of complexing a transition metal cation. The polymeric beads are named as magnetic ion-exchange resin. Taiwan Patent Application No. 094108928 further discloses the separating method of transition metal ions and other ions from water solution by using this ion-exchange resin.

There are many examples that the magnetic ion-exchange resins are achieved by polymerizing magnetic particles (generally nanometer level) with a monomer and then forming polymer particles. The conventional oil in water suspension polymerization method includes the following: a monomer, magnetic nano-metal particles (iron oxide, $Fe_3O_4$, for example), an initiator, a solvent and as on fully dispersed, then are emusified to suspend in a organic phase, mixed into a water phase, finally magnetic particles are fully dispersed in an interior of magnetic polymer particles are obtained, and further the magnetic polymer particles are chemical bonded with positively charged or negatively charged ionic functional groups. Another method as disclosed in Korean patent No. KR 20040091385 comprises steps of: dispersing an organic layer consisting of magnetite, monomer and a cross-linking agent in water under nitrogen atmosphere; and after adding a polymerizable surfactant having a quaternary ammonium group and an initiating agent to the dispersion, performing a suspension polymerization to obtain a magnetic anion-exchange resin.

In addition to the conventional suspension polymerization method, the so-called spray suspension polymerization method can also be used by for example, Yang et al. This method includes the steps of applying the water solution having polyvinyl alcohol (PVA) as a water phase, and the monomer with methyl methacrylate and divinylbenzene, iron oxide ($Fe_3O_4$) coated with oleic acid, benzoyl peroxide and so on as the oil phase, under the spray of droplets in nitrogen atmosphere, forming magnetic polymer particles after polymerization, and finally obtaining a magnetic anion-exchange resin after introducing the surface amino-modification. (Yang et al., Appl. Microbiol. Biotechnol. 72 (2006) 616-622).

Heeboll-Nielsen et al. suggested a variety of production methods (Heeboll-Nielsen et al., J. Bioetchnol. 113 (2004) 247-262). One of typical methods includes providing a magnetic metal material as a core, then coating a polymer with ion-exchange function to its outer surface to form a shell. The method of China Patent No. 1680469A includes heating a thermoplastic organic polymer to molten state, mixing with magnetic particles into uniformly cross-mixing molten slurry, and then the molten slurry into the micro-droplets through pores, the micro-droplets pass through floating active elements within the ion-exchange resin, and finally collecting grains as magnetic ion-exchange resin.

Conversely, ion-exchange resin can be used as a core particle covered with a magnetic material, thereby obtaining a magnetic ion-exchange resin. For example, U.S. Pat. No. 5,595,666 A and U.S. Pat. No. 5,652,190 A disclose a weak anion exchange resin (polyamine-epichlorohydrin resin) which is covered with magnetic material ($M_2O_2$), wherein one M is iron, and the other M can be iron, barium, magnesium, calcium or similar elements. An ion-exchange resin made of cross-linking agarose also can adsorb magnetic nano-particles to form a magnetic ion-exchange resin (Nixon, et al., Chem. Mater., 4 (1992) 117-121). Zhang et al. suggests a method includes the steps of: manufacturing about 1 μm of cross-linked polymer microspheres (wherein the monomer is polyglycidyl methacrylate (PGMA) and the cross-linker is divinylbenzene), reacting with ethylenediamine to form the positively charged anion exchange resin, soaking into the solution of ferrous iron and ferric iron ($FeCl_3$ and $FeSO_4$), precipitating iron oxide under alkaline conditions depositing onto the anion exchange resin surface, and finally obtaining a magnetic anion exchange resin which can capture DNA (Zhang et al., J. Chromatogr. B, 877 (2009) 127-133).

In addition, U.S. Pat. No. 5,855,790 discloses a more complex method to produce magnetic particles which comprises a core of a magnetic material surrounded by a mixture of cellulous fibers and a solid binder to form a solid block of polymer. The solid block is then ground to create small particles. The iron core with its cellulose coating provides strength to the ground particles which are then functionalised. The US patent also provides an alternative method in which the polymerisation is conducted with the particles dispersed in oil, which thus creates discrete, round particles of controlled size.

Another method for manufacturing a composite magnetic ion-exchange resin includes the steps of: mixing nanosized magnetic material (such as magnetite), ion-exchange resin and polymer substrate with an appropriate solvent, spray-drying into composite particles of a magnetic ion-exchange resin, wherein the polymer substrate plays the role of bonding magnetic material and ion-exchange resin (Hickstein and Peuker, Biotechnol Prog. 24 (2008) 409-416; Kappler et al., J. Biosci. Bioeng. 105 (2008) 579-585).

U.S. Pat. No. 6,718,742 discloses a simpler method of mixing the magnetic particles (iron oxide, $Fe_3O_4$) of 5 μm or less with the granular, porous polymethacylate carboxyl ion-exchanger (negatively charged), and finally achieving a magnetic ion-exchange resin used to extract DNA. This magnetic ion-exchange resin makes the magnetic particles entrapped therein by using pore features of the polymer microspheres. Consequently, the magnetic particles easily escape from the pores of magnetic ion-exchange resin during application.

JP 2001272395 discloses a magnetic ion-exchange resin is used to separate histamine from blood, wherein histamine is quantified after desorbed from the magnetic ion-exchange resin, and then the levels of histamine in blood are learned. WO 2006/059655 provides that the mixture use of ion-exchange resin and magnetic particles can separate a microorganism or cells from samples, and extract a nucleic acid from the microorganism or the cells. Magnetic ion-exchange composites are made from the mixture of substrate, magnetic material and ion-exchange resin at a certain ratio to form amorphous particles, which were used to separate proteins (Kappler et al., J. Biosci. Bioeng. 105 (2008) 579-585).

The conventional manufacturing method of nanoscale magnetic ion-exchange resin is using nanoscale magnetic materials as a core, incorporating ion-exchange functional groups by chemical modification, and finally obtaining nano-scale magnetic ion-exchange resin. CN 1699447A discloses that iron oxide ($Fe_3O_4$) and polyacrylic acid form a covalent bond in the activation of carbonized dihydrazide, and magnetic cation-exchange resin is obtained. Negatively charged nano-magnetic ion exchange resin synthesized by binding carboxymethylated chitosan (CMCH) covalently on the surface of $Fe_3O_4$ nano-particles can be applied to separating protein (Yang et al., Ind. Eng. Chem. Res. 48 (2009) 944-950).

However, particle diameter of the above magnetic ion-exchange resins can affect the collection time, wherein the smaller particle diameter will induce the longer collection time. The conventional nanoscale ion-exchange resin has longer collection time that is impractical for biological magnetic separation. Thereby, it is necessary in the industrial development for developing a magnetic ion-exchange resin for quick separation and purification of biological molecules.

SUMMARY OF THE INVENTION

As mentioned above, the conventional method for manufacturing magnetic ion-exchange resin is more complex, and the magnetic particles are easily detached therefrom and have low collection efficiency due to small particle diameter. The present invention provides a method for preparing a magnetic ion-exchange polymer microspheres comprises the steps of:

(a) preparing ion-exchange polymer microspheres, and immersing the ion-exchange polymer microspheres into a solution in order to swell the ion-exchange polymer microspheres, and the ion-exchange polymer microspheres are made of polystyrene, or a copolymer including styrene and at least one monomer, wherein the polystyrene or the copolymer forms a network structure of polymer chains by adding a cross-linking agent, and the solution allows the network structure of polymer chains to swell and expand;

(b) adding a colloid solution containing magnetic nano-particles into the solution to form a mixture and adjusting the pH value of the mixture to 8-12 in order to allow the magnetic nano-particles to enter into the network structure of polymer chains; and;

(c) separating the ion-exchange polymer microspheres from the solution, wherein the ion-exchange polymer microspheres are non-porous, and the ion-exchange polymer microspheres shrink after removing the solution to allow the network structure of polymer chains to become compact, then the magnetic nano-particles are entrapped within the network structure of polymer chains.

The present invention also provides a magnetic ion-exchange microsphere resin prepared by the method of the present invention.

In addition, the magnetic ion-exchange microsphere resin of the present invention can efficiently separate biomolecules such as the separation and purification of DNA from the cell crude extract, and can be applied to immobilize enzyme and protein for the enzymatic conversion. Therefore, the present invention provides a method of separating biomolecules or cells form mixtures containing them by using the above magnetic ion-exchange microsphere resin, wherein the biomolecules are selected from the group consisting of DNA, RNA, antibodies, antigens, proteins and nucleic acids.

Taiwan Pat. No. I277632 and U.S. Pat. No. 7,754,278B2 disclose magnetic polymer microspheres and the method for the preparation thereof, wherein the magnetic polymer microspheres are obtained by magnetic nano-particles penetrated into the swelling polymer microspheres. Further, the charged functional groups are introduced onto the surfaces thereof by chemical modification to obtain a magnetic ion-exchange resin. During the surface chemical modification, strong acid, alkali or solvents are generally used, and thus magnetic nano-particles will leak out or be dissolved out. For example, strong sulfuric acid and nitric acid are required in manufacturing sulfonic acid cation exchange resin, which leads to the leakage of magnetic nano-particles within polymer microspheres and significant reduction of the magnetic properties of polymer microspheres. Moreover, the methods of TW I277632 and U.S. Pat. No. 7,754,278B2, the neutral solution is used during the magnetic nano-particles are adsorbed into the swelled polymer microspheres (polystyrene or a copolymer including styrene as one of monomers), which has small effect on the pH value of solution. On the contrary, during the magnetic nano-particles are adsorbed into the swelled ion-exchange polymer microspheres, the pH value of the solution is obviously effected because of polymer microspheres having charged functional groups. As a result, in the present invention, the more amounts of magnetic nano-particles are adsorbed in ion-exchange resin by adjusting the pH value.

Additionally, as disclosed in U.S. Pat. No. 6,718,742, magnetic particles are mixed with the porous ion-exchange resin, and are apt to leak out because of the magnetic particles only being trapped in the pores. However, in the present invention, the neutral polar solvent is used to swell out polymer chains of ion-exchange resin, the nano-particles are penetrated therein after removing the solvent and the magnetic nano-particles are firmly entrapped within the cross-linking polymer chains, which can avoid the leakage mentioned above.

Examples of the present invention are further illustrated with the implementation of the following figures. For the person skilled in the art, it is known that these examples are only used to explain the present invention and not to limit the scope of the present invention. Any modification and changes are considered as being in the scope and range of the present invention. Thus, the protection scope of the present invention is defined by the following contents.

DETAILED DESCRIPTION

Figure 1:
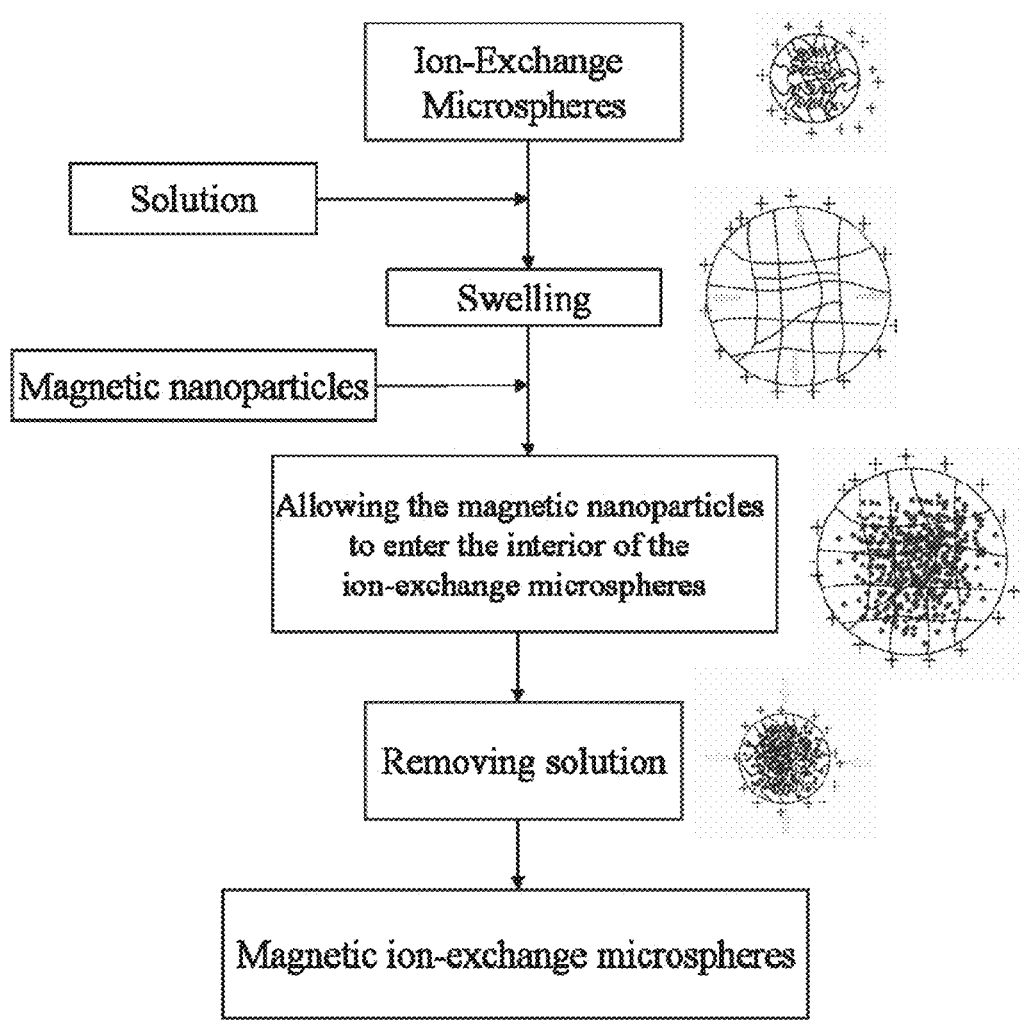
FIG. 1 is a flow diagram for a method for preparing magnetic ion-exchange polymer microspheres of the present invention.

FIG. 1 is a flow diagram for a method for preparing magnetic ion-exchange polymer microspheres of the present invention. The present invention provides a method comprising: preparing ion-exchange polymer microspheres which can be pre-prepared or purchased, and immersing the ion-exchange polymer microspheres into a solution in order to swell a network structure of polymer chains from the ion-exchange polymer microspheres, and the solution allows the network structure of polymer chains to swell and expand. Secondly, the magnetic nano-particles are added into the ion-exchange resin solution and fully dispersed therein. Then, the magnetic nano-particles enter into the network structure of polymer chains of ion-exchange resin.

Finally, the ion-exchange resin is removed from the solution, and the magnetic nano-particles unabsorbed by ion-exchange resin are washed away, the solution covering the magnetic ion-exchange resin is further removed by air drying, vacuum drying or any other known methods applied to remove solutions. At this time, the ion-exchange resin shrinks without solution to swell. The magnetic magnetic particles previously entering into the network structure of the polymer chains are entrapped therein due to the network structure of the polymer chains shrinking, the magnetic magnetic particles are embedded in the ion-exchange resin, and thereby the magnetic ion-exchange resin of the present invention is obtained.

The particle diameters of the ion-exchange polymer microspheres used in the present invention are not especially limited, as long as the particle diameters of the ion-exchange polymer microspheres are larger than those of the magnetic nano-particles, but they are preferably from submicrons to microns, that is, between 0.1 µm and 1 mm. There are no particular restrictions regarding the kinds of the polymer particles used in the present invention, and the polymer particles can be prepared by different polymerization methods, preferably polystyrene or a copolymer containing styrene and at least one monomer, wherein the copolymer further includes a vinyl monomer with at least one functional group, the polymer chains of the copolymer are cross-linked to form a network structure, the preferred cross-linking agent is divinylbenzene (DVB).

There are no particular limits in charged functional groups bonded with the ion-exchange polymer microspheres, which can be positively charged (anion exchange resin) or negatively charged (cationic exchange resin).

Moreover, the ion-exchange polymer microspheres are preferably non-porous, or the pore sizes of the ion-exchange polymer microspheres are smaller than the particle diameters of the magnetic nano-particles so that the magnetic nano-particles entrapped within the network structure of polymer chains formed by ion-exchange polymer microspheres of the present invention cannot run off. However, those having ordinary skill in the art will appreciate that the pore sizes of the ion-exchange polymer microspheres can be larger than the particle diameters of the magnetic nano-particles.

Furthermore, the magnetic nano-particles used in the present invention are not especially limited, and any magnetic nano-particles made by the conventional methods can be used. However, if the magnetic nano-particles having relatively high magnetization are used, the magnetic polymer microbeads having relatively high magnetization can be produced. Moreover, if the concentration of the magnetic nano-particles is high, the number of the magnetic nano-particles encapsulated by the polymer particle is increased. That is, the number of the magnetic nano-particles entrapped within per unit volume of the network structure of the ion-exchange polymer microsphere is increased. Therefore, the magnetic polymer microbeads having relatively high magnetization can be obtained. Furthermore, if the magnetic nano-particles entrapped within the network structure of the ion-exchange polymer microspheres are superparamagnetic, the obtained magnetic ion-exchange polymer microspheres are also superparamagnetic. Moreover, the materials of the magnetic nano-particles used in the present invention are not especially limited, and these materials include, but not limited to, iron oxide, ferromagnetic oxide, ferromagnetic nickel, ferromagnetic cobalt, iron-cobalt-nickel alloy, iron carbide (FeC), and iron-platinum (FePt) alloy. The above-mentioned iron oxide includes, but not limited to, $Fe_3O_4$, $Fe_2O_3$. The above-mentioned ferromagnetic oxide includes, but not limited to, $MnZnFe_2O_4$, $NiZnFe_2O_4$.

The solution used in the present invention can allow the ion-exchange polymer microspheres to swell, but not to be dissolved therein, and as well it can allow the magnetic nano-particles to be evenly dispersed therein. The solution includes a neutral polar solvent which is miscible with water and most of the organic solvents. Examples of the solution include, but are not limited to, a single solvent, a mixture of several solvents, or a mixture of solvents and water. The solvent preferably has low biotoxin, and the polar parameter of Hansen solubility parameters of the solvent is preferably between 2 and 12 $(cal/cm^3)^{1/2}$, and more preferably between 5 and 9 $(cal/cm^3)^{1/2}$, and the hydrogen bonding parameter thereof is preferably between 2 and 8 $(cal/cm^3)^{1/2}$, and more preferably between 3 and 6 $(cal/cm^3)^{1/2}$. The solvents used in the present invention are preferably dipolar aprotic solvents, and examples of the solvents include, but are not limited to, dimethylsulfoxide (the value of the polar parameter is 8.0 $(cal/cm^3)^{1/2}$, and the value of the hydrogen bonding parameter is 5.0 $(cal/cm^3)^{1/2}$), N-methyl-2-pyrrolidone (the value of the polar parameter is 6.0 $(cal/cm^3)^{1/2}$, and the value of the hydrogen bonding parameter is 3.5 $(cal/cm^3)^{1/2}$), dimethylformamide (the value of the polar parameter is 6.7 $(cal/cm^3)^{1/2}$, and the value of the hydrogen bonding parameter is 5.5 $(cal/cm^3)^{1/2}$), and dimethylacetamide (the value of the polar parameter is 5.6 $(cal/cm^3)^{1/2}$, and the value of the hydrogen bonding parameter is 5.0 $(cal/cm^3)^{1/2}$).

The following examples 1 and 2 are used to explain the method for preparing magnetic ion-exchange polymer microspheres in accordance with the present invention. Example 4 is used to compare the effects of various initial concentrations of magnetic particles to particle diameters of the final particles and separation time of adsorbed material. In addition, Examples 3, 5 and 6 illustrate the results of the use of magnetic ion-exchange microspheres for the separation and purification of DNA and enzyme immobilization, thus the magnetic ion-exchange polymer microspheres of the present invention can be applied in many areas, and thereby they have high economic value.

EXAMPLE 1

The Method for Manufacturing the Magnetic Ion-Exchange Resin and the Effect of pH Value to Diffusion 0.25 g of anion exchange resin (Lewatit® MonoPlus M500 or Lewatit® MonoPlus MP64) is immersed into a solution which is consisting of N-methyl pyrrolidinone (NMP, polarity parameter value (Hansen) is 6.0 $(cal/cm^3)^{1/2}$ and hydrogen bonding parameter value is 3.5 $(cal/cm^3)^{1/2}$) mixed with water in the conical flask at volume ratio (v/v) of 3:4 i.e. 15 ml of NMP and 20 ml of water, is fully dispersed by sonication. Then placed in the constant temperature shaker incubator at 200 rpm for 24 hours at 25° C. to swell.

In the example, two ion exchange resins: Lewatit® MonoPlus M500 and Lewatit® MonoPlus MP64 are polystyrene crosslinked with divinylbenzene. The surface functional group of Lewatit® MonoPlus M500 is -[Ph-$(CH_2)$—$N(CH_3)_3$]$^+$, the diameter is 0.62 mm Lewatit® MonoPlus MP64 is a weak alkaline anion exchange resin, and the surface functional group thereof is the quaternary amine, and the particle diameter thereof is 0.59 mm.

In addition, the chemical coprecipitation method for manufacturing magnetic nano-particles includes the steps of: mixing ferrous iron and ferric iron at the molar ratio of 1:2; stirring at the speed of 300 rpm; adjusting the pH value of reactants by the use of 1M sodium hydroxide (NaOH) solution to 12; reacting at 60° C. for 1 hour and then cooling by ice bath; extracting black precipitates under the centrifugal rotation speed of 3,000 rpm (approximately 2,500 g); immersing this precipitates into 1N hydrogen chloride (HCl) solution for 1.5 hours; extracting precipitates by the centrifugal rotation; adding deionized water to disperse; and finally obtaining magnetic nano-particles ($Fe_3O_4$) with the particle diameter of about 10 nm.

2.5 ml the above solution containing $Fe_3O_4$ magnetic nano-particles is added into the above solution containing anion exchange resin to obtain a mixture, and the concentration of the mixture is 10 mg/ml and pH value thereof is from 3 to 12. Furthermore, the mixture is placed in a shaker incubator at 200 rpm for 2 days at 30° C., in order to make magnetic nano-particles enter into anion exchange resin. The excess solvent is removed by exhaust filter, and then particles are rinsed three times and dried by air to obtain a magnetic anion exchange resin.

Figure 2:
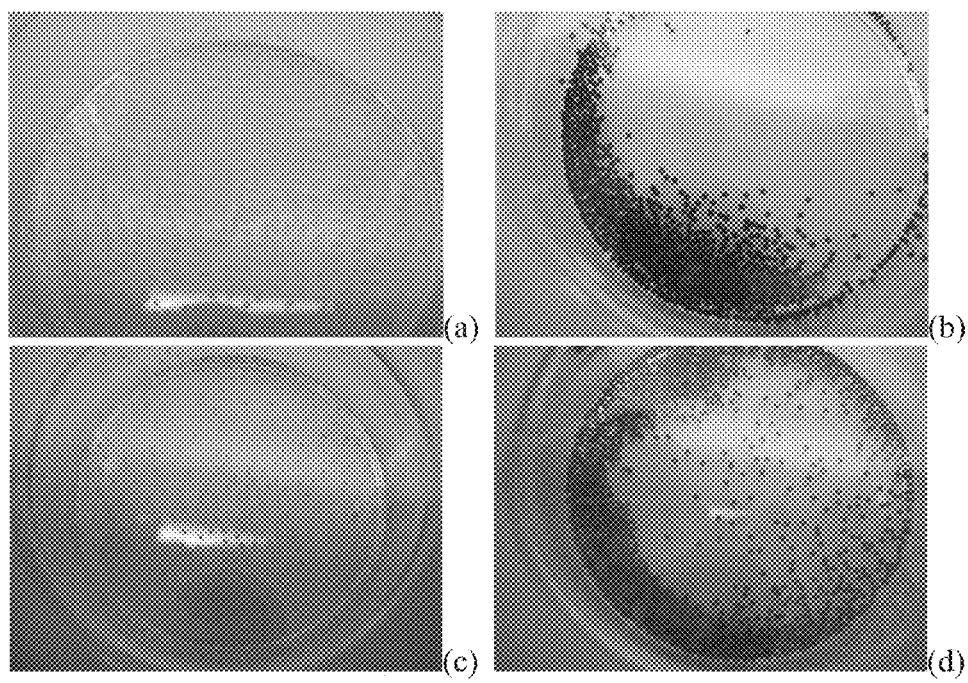
FIG. 2(a) is a photograph of an anion exchange resin Lewatit® MonoPlus M500.
FIG. 2(b) is a photograph of a magnetic anion exchange resin prepared from anion exchange resin Lewatit® MonoPlus M500 in Example 1.
FIG. 2(c) is a photograph of an anion exchange resin Lewatit® MonoPlus MP64.
FIG. 2(d) is a photograph of a magnetic anion exchange resin prepared from anion exchange resin Lewatit® MonoPlus MP64 in Example 1.

FIG. 2 illustrates the photographs of anion exchange resins Lewatit® MonoPlus M500 and Lewatit® MonoPlus MP64 before and after treated by the above method. Referring to FIGS. 2(b) and 2(d), the two anion exchange resins are immersed in NMP solution for 24 hours and then immersed and swelled in $Fe_3O_4$ magnetic nano-particles solution for 2 days. In the end, the obtained magnetic ion-exchange resins after being rinsed and dried by air have partial black color, which confirms that magnetic nano-particles have entered into ion-exchange resin. Because of the pores of the ion-exchange resin being interconnected, magnetic nano-particles entering into ion-exchange resin are apt to leak out thereof. Thus, the magnetic nano-particles of the magnetic ion-exchange resin in the present invention are located in the network structure of polymer chains, instead of the magnetic nano-particles of prior arts are located in the pores of polymer particles.

Figure 3:
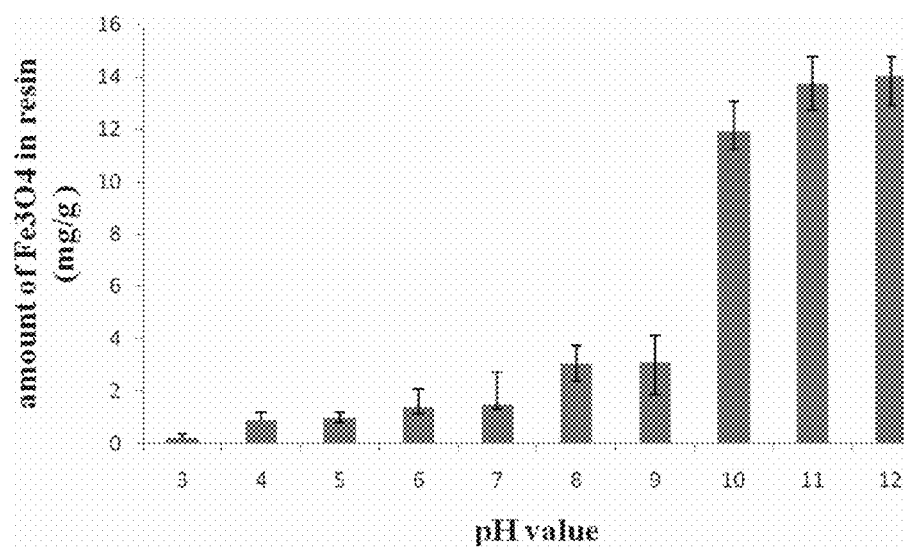
FIG. 3 shows the effect of pH value of solution to the diffusion of $Fe_3O_4$ nano-particles into ion-exchange resin of Lewatit® MonoPlus M500.

To know the effect of pH value to the diffusion of $Fe_3O_4$ nano-particles into ion-exchange resin, the amounts of iron oxide ($Fe_3O_4$) particles diffusing into the anion exchange resin Lewatit® MonoPlus M500 at various pH values are measured by atomic absorption spectroscopy (AAS) (as shown in FIG. 3). Referring to FIG. 3, the diffusion amounts (i.e., the amount of $Fe_3O_4$ particles diffusing into the anion exchange resin) changes with pH values, and the pH value is obviously effect the diffusion amount of $Fe_3O_4$ particles entered into the interior of the ion-exchange resin. The amount of Fe3O4 particles contained in anion exchange resin did not significantly increase at a pH value less than 7, the amount thereof at pH value of 8-9 has a two to three times increase than that at acidic condition, and the amount thereof at pH value of 10-12 has a eight to nine times increase than that at acidic condition. As a result, the diffusion occurs under strong alkaline condition. It is concluded that isoelectric point of $Fe_3O_4$ is about pH 6.8. When pH value more than 7, $Fe_3O_4$ is negatively charged and easily attaches to the anion exchange resin Lewatit® MonoPlus M500 for easily diffusing therein in the acidic condition. When pH value more than or equal to 10, $Fe_3O_4$ particles is highly negatively charged and easily diffused into an interior of the anion exchange resin Lewatit® MonoPlus M500.

EXAMPLE 2

Effect of Initial Concentration of Magnetic Particles to the Diffusion Amount 0.25 g of anion exchange resin (Lewatit® MonoPlus M500 or Lewatit® MonoPlus MP64) or cation exchange resin (Lewatit® MonoPlus S100) is immersed into a solution which is consisting of N-methylpyrrolidinone mixed with water in the conical flask at volume ratio (v/v) of 3:4, i.e., 15 ml of NMP and 20 ml of water, is fully dispersed by sonication. Then placed in the constant temperature shaker incubator at 200 rpm for 24 hours at 25° C. to swell.

In this example, Lewatit® MonoPlus S100 is cross-linked polystyrene. The surface functional group of Lewatit® MonoPlus S100 is sulfonic acid, the diameter is 0.315~1.25 mm, and the appearance thereof is transparent light brown.

After that, the concentrations of 2.5 ml $Fe_3O_4$ solution of example 1 added thereto are 2.5, 5, 7.5, or 10 mg/ml respectively, and pH value thereof is adjusted to 12. The obtained mixture is immersed in shaker incubator at 200 rpm for 2 days at 30° C., in order to make magnetic nano-particles adsorbed into ion-exchange resin. The excess solvent is removed by exhaust filter, and then particles are washed three times and dried by air to obtain a magnetic ion-exchange resin.

Figure 4:
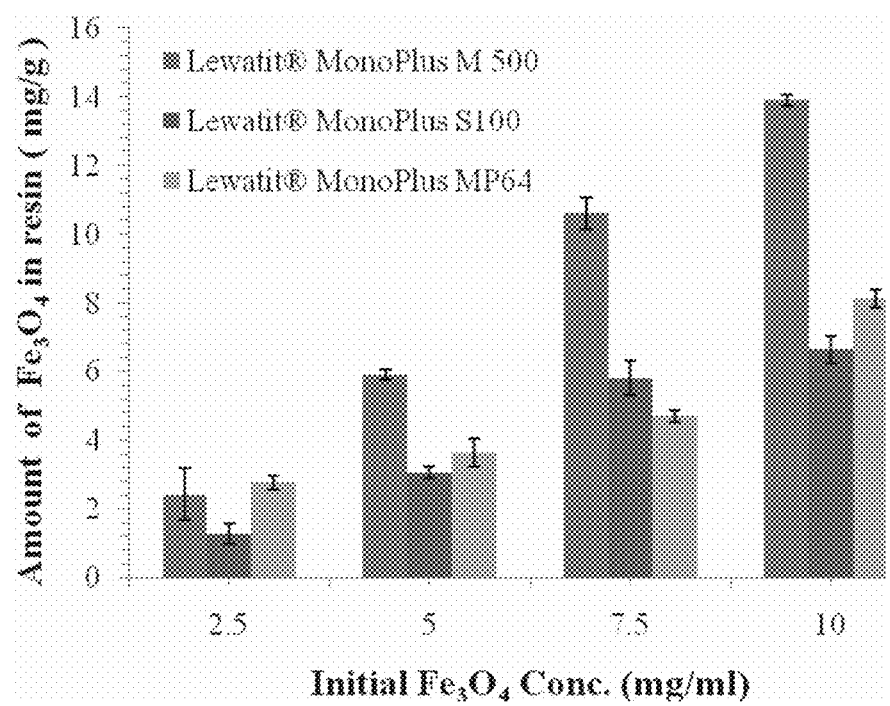
FIG. 4 shows the amount of $Fe_3O_4$ entrapped within the ion-exchange resin changing with the initial concentration of $Fe_3O_4$.

To know the relationship between the amount of $Fe_3O_4$ adsorbed by ion-exchange resin and the initial concentration of $Fe_3O_4$ solution, the amount of $Fe_3O_4$ entrapped within three ion-exchange resin (Lewatit® MonoPlus M500, Lewatit® MonoPlus MP64, and Lewatit® MonoPlus S100 separately employed) under various initial $Fe_3O_4$ concentrations is measured by atomic absorption spectroscopy (AAS). FIG. 4 shows the amount of $Fe_3O_4$ entrapped within the ion-exchange resin changed with the initial concentration of $Fe_3O_4$. Referring to FIG. 4, the amount of $Fe_3O_4$ contained in ion-exchange resin increased with the initial concentration of $Fe_3O_4$ incubated with the ion-exchange resin. The amount of $Fe_3O_4$ contained in ion-exchange resin is 6.63±0.27 mg/g obtained from the initial concentration of 10 mg/ml cation-exchange resin Lewatit® MonoPlus S100, and the amount of $Fe_3O_4$ contained in ion-exchange resin is 8.12±0.38 mg/g obtained from the initial concentration of 10 mg/ml ion-exchange resin Lewatit® MonoPlus MP64. Finally, the amount of $Fe_3O_4$ contained in Lewatit® MonoPlus M500 is 13.9±0.17 mg/g, and the saturation magnetization thereof is 1.68 emu/g.

The example illustrates that the higher initial concentration of $Fe_3O_4$, the higher amount of magnetic material contained in magnetic ion-exchange resin, and the shorter time of separating ion-exchange resin from the solution in magnetic field. As a result, the time of separating magnetic Lewatit® MonoPlus M500 obtained from the initial concentration of 10 mg/ml $Fe_3O_4$ is shortest in magnetic field, i.e., about one second (using MAFSiMAG™ Seperator from Millitenyi Biotec's company).

EXAMPLE 3

Separate Plasmid DNA by Using the Magnetic Ion-Exchange Resin of the Present Invention

*E. coli* containing the plasmid pEGFP-C1 were inoculated into 30 ml LB medium (containing 100 μg/ml kanamycin) and placed in shaker incubator at 150 rpm for 16-18 hours at 37° C. And then the broth culture of *E. coli* was added to a conical flask having 250 ml LB medium (containing 100 μg/ml kanamycin) at 150 rpm overnight at 37° C. The above broth culture of *E. coli* was added to a conical flask having 3 L LB medium (containing 100 μg/ml kanamycin) at 150 rpm for 5 hours at 37° C. After that, the supernatant is removed at 4° C. by the centrifugation speed of 12000 rpm for 20 minutes. The pellet was added to 84 ml G/T/E buffer (50 mM glucose, 10 mM EDTA, 25 mM Tris-HCl and 144 mg lysozyme, pH=8.0), completely mixed and then incubated on ice for 20 minutes. Thereby, 144 ml freshly prepared NaOH/SDS cold denaturation solution (0.2 N NaOH and 1% SDS) was added thereto and fully mixed and incubated on ice for 10 minutes. 90 ml of 3 M sodium acetate (pH=5.0) was added thereto and mixed and incubated on ice for 20 minutes. Finally, the supernatant collected at 4° C. by the centrifugation speed of 10000 rpm for 20 minutes is the cell crude extract.

10 mg of magnetic ion-exchange resin (obtained by immersing ion-exchange resin Lewatit® MonoPlus M500 in 10 mg/ml magnetic nano-particles solution and pH value thereof being adjusted to 12) in accordance with example 1 was fully mixed with 1 ml the cell crude extract and 1 ml binding buffer (10 mM Tris-HCl, 1 M NaCl, 1 mM EDTA, pH=6.5) for 5 minutes. The mixture was selectively adsorbed and separated from magnetic nano-particles by using Millitenyi Biotec's magnetic base MAFSiMAG™ Seperator. The supernatant was removed after washing three times by 2 ml washing buffer (10 mM Tris-HCl and 1 mM EDTA, pH=8). The purified plasmid DNA solution was obtained after detachment twice by adding to 1 ml desorption buffer (1.5 M NaCl, 0.01 M Tris-HCl, 1 mM EDTA, pH=9.0). Table 1 shows $Abs_{260}/Abs_{280}$ ratio, protein concentration, RNA concentration and DNA concentration to the supernatant before purification (i.e., the supernatant of the cell crude extract), adsorbing residual solution, first washing supernatant, second washing supernatant, third washing supernatant, first desorption solution, second desorption solution (wherein $Abs_{260}$ is measured DNA concentration, $Abs_{280}$ is measured protein concentration, thus the higher $Abs_{260}/Abs_{280}$ ratio, the higher DNA purity).

With 10 mg ion-exchange resin Lewatit® MonoPlus M500 selected as control group, results of the purified plasmid DNA separated from the cell crude extract by the above method is showed in Table 2.

Figure 5:
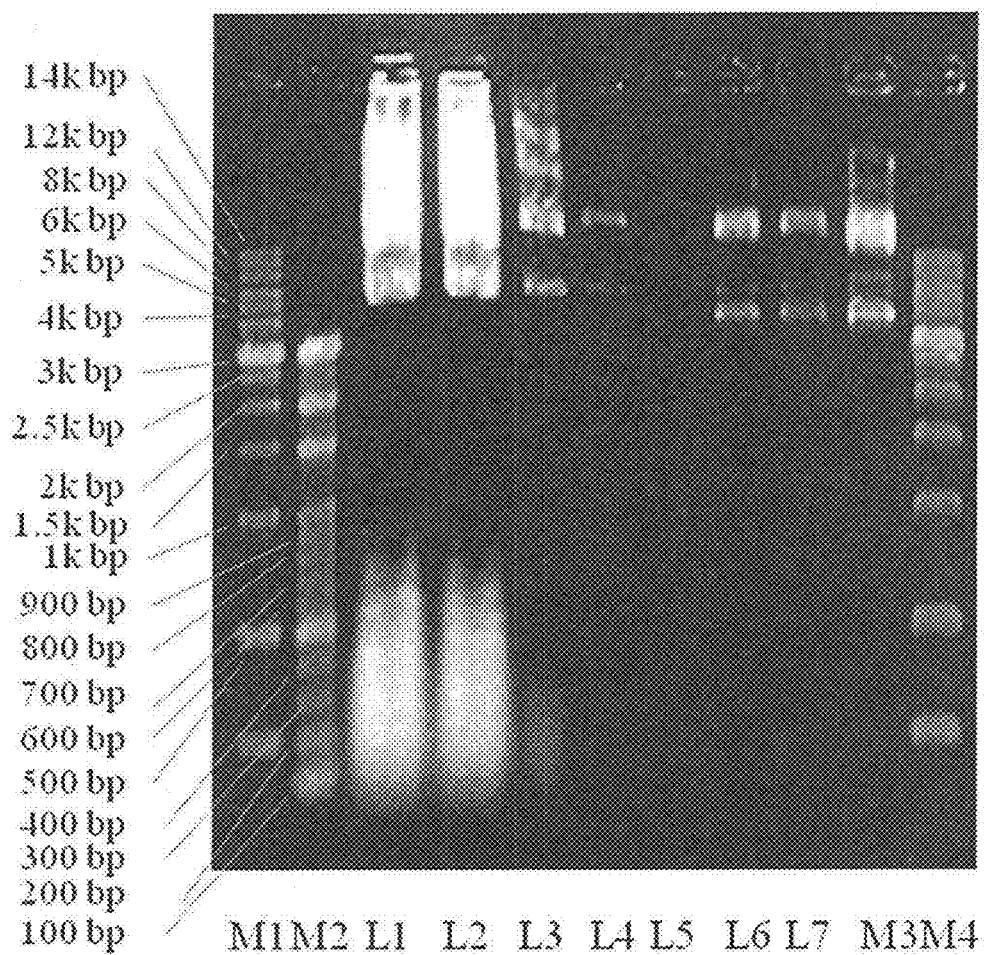
FIG. 5 shows agar gel electrophoresis of DNA obtained from different separation step by using a magnetic ion-exchange resin (prepared from Lewatit® MonoPlus M500), wherein M1: marker (200-14000 bp), M2: marker (100-3000 bp), L1: cell crude extract, L2: residual adsorption solution, L3: the first solution, L4: the second solution, L5: the third solution, L6: the first desorption solution, L7: the second desorption solution, M3: pure plasmid pEGFP-C1, M4: DNA marker (200-14000 bp).

$Abs_{260}/Abs_{280}$ ratio is measured by NanoDrop 1000 spectrophotometer, RNA concentration is measured by Qubit fluorometer and protein concentration is measured by Bradford Protein Assay method. As shown in Table 1, $Abs_{260}/Abs_{280}$ ratio of the cell crude extract is 2.17, after purification, $Abs_{260}/Abs_{280}$ ratios of first desorption solution and second desorption solution reduce to about 1.80. RNA concentration reduces to less than 1 μg/ml and protein concentration reduces to less than 2 μg/ml. As shown in Table 2 of the results of purified DNA in use of non-magnetic Lewatit® MonoPlus M500 shown in, final $Abs_{260}/Abs_{280}$ ratio is 1.94. In this instance, the RNA concentration reduces to less than 6 μg/ml and protein concentration reduces to less than 5 μg/ml. A comparison of data in Table 1 and Table 2 indicates that the purity in use of magnetic ion-exchange resin is higher than that in use of non-magnetic ion-exchange resin. As shown in FIG. 5, RNA and DNA fragments were separated from the cell crude extract by a series of purification steps. Measured from the total amounts of first desorption solution and second desorption solution, the amount of selectively adsorbed plasmid DNA by magnetic ion-exchange resin is 4.68 mg/g, and non-magnetic ion-exchange resin is 3.93 mg/g, which results from completely recovered magnetic ion-exchange resin.

The effect of a magnetic ion-exchange resin of the present invention is superior, the addition of magnetic nano-particles has no effect on ion-exchange function thereof, and DNA selective adsorption is applied to separate and purify in the use of surface functional groups. At the same time, the magnetic ion-exchange resin has a stable property, and magnetic material is not apt to leak out in applications.

TABLE 1 the results of purification DNA from a magnetic anion exchange resin
(manufactured from Lewatit ® MonoPlus M500, 10 mg)

| Solution | $Abs_{260}/Abs_{280}$ | Protein concentration (μg/ml) | RNA concentration (μg/ml) | DNA amount (μg) |
|---|---|---|---|---|
| Supernatant of the cell crude extract | 2.17 | 114.7 ± 1.61 | 648 | 628.27 ± 8.56 |
| adsorbing residual solution | 2.18 ± 0.026 | 80.6 ± 1.06 | 579.2 | 547.6 ± 4.92 |
| $1^{st}$ washing supernatant | 2.09 ± 0.085 | 17.26 ± 0.53 | 68.4 | 28.2 ± 1.31 |
| $2^{nd}$ washing supernatant | 1.9 ± 0.59 | 7.79 ± 2.15 | 8.7 | 3.33 ± 1.74 |
| $3^{rd}$ washing supernatant | 1.46 ± 0.32 | 6.82 ± 2.11 | N/A | 2.4 ± 1.15 |
| $1^{st}$ desorption solution | 1.79 ± 0.57 | 0.51 ± 0.15 | 0.576 | 30.77 ± 5.7 |
| $2^{nd}$ desorption solution | 1.8 ± 0.45 | 1.21 ± 0.53 | 0.5 | 16 ± 1.87 |

TABLE 2 the results of purification DNA from a non-magnetic anion exchange resin
(Lewatit ® MonoPlus M500, 10 mg)

| Solution | $Abs_{260}/Abs_{280}$ | Protein concentration (μg/ml) | RNA concentration (μg/ml) | DNA amount (μg) |
|---|---|---|---|---|
| Supernatant of the cell crude extract | 2.2 ± 0.02 | 112.56 ± 3.7 | 462 | 635.43 ± 17.82 |
| Adsorbing residual solution | 2.15 ± 0.03 | 76.62 ± 1.04 | 365.2 | 542.37 ± 11.4 |
| $1^{st}$ washing supernatant | 2.08 ± 0.09 | 18.76 ± 0.3 | 24.2 | 28.7 ± 1.69 |
| $2^{nd}$ washing supernatant | 1.57 ± 0.68 | 6.35 ± 1.29 | 25 | 3.56 ± 1.96 |
| $3^{rd}$ washing supernatant | 0.99 ± 0.37 | 1.34 ± 0.36 | N/A | 2.1 ± 1.01 |
| $1^{st}$ desorption solution | 1.94 ± 0.04 | 4.28 ± 0.77 | 5.66 | 27.4 ± 2.29 |
| $2^{nd}$ desorption solution | 1.94 ± 0.1 | 4.61 ± 1.27 | 5.74 | 11.9 ± 2.8 |

EXAMPLE 4

Effects of Various Concentrations of Magnetic Particles to Particle Diameters of the Final Products and Separation Time of Adsorbed Material As the process of Example 1, 0.25 g polystyrene-divinylbenzene particles (Sigma 538736-5G, 100-200 mesh, 1% crosslinked divinylbenzene) bonded with diisopropylamine were used as an anion exchange resin with particle diameter of 75-150 μm. The anion exchange resin is immersed into a solution which is consisting NMP mixed with water in the conical flask at volume ratio (v/v) of 3:4, i.e., 15 ml of NMP and 20 ml of water, is fully dispersed by sonication. Then placed in the constant temperature shaker incubator at 200 rpm for 24 hours at 25° C. to swell.

After that, the concentrations of 2.5 ml $Fe_3O_4$ solution of Example 1 added thereto are 5 or 10 mg/ml respectively, and pH value thereof is adjusted to 12. The obtained mixture is immersed in shaker incubator at 200 rpm for 2 days at 30° C., in order to make magnetic nano-particles adsorbed into ion-exchange resin. The excess solvent is removed by exhaust filter, and then particles are washed three times and dried by air to obtain a magnetic anion-exchange resin.

Figure 6:
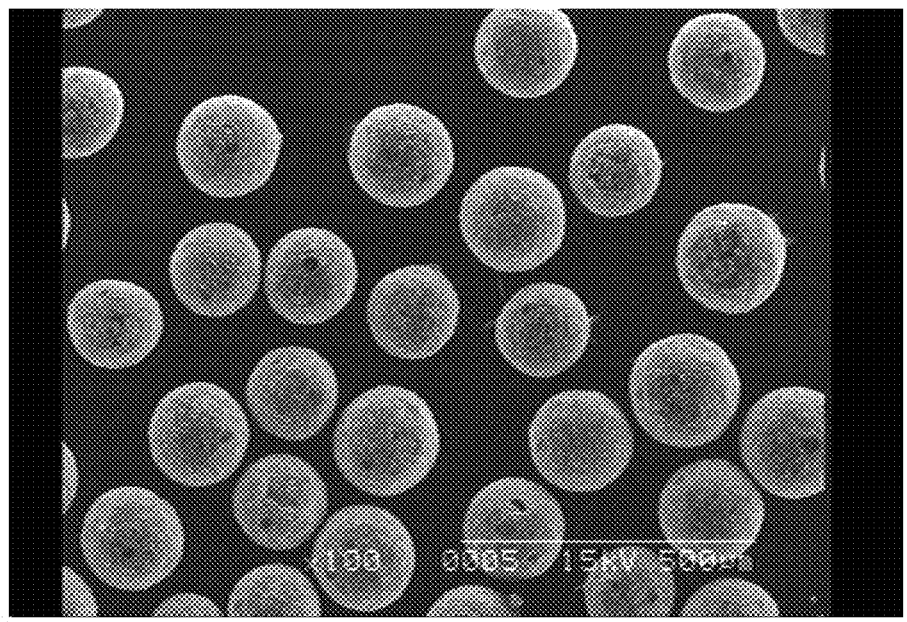
FIG. 6 is a scanning electron microscope photograph of a magnetic ion-exchange resin manufactured by using 5 mg/ml nanoscale magnetic iron oxide ($Fe_3O_4$) solution.
Figure 7:
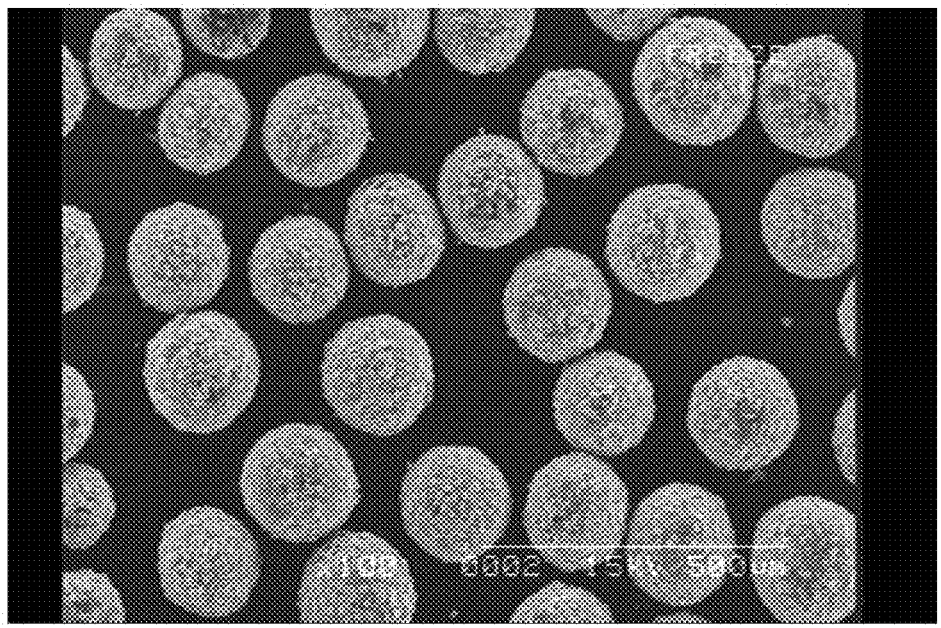
FIG. 7 is a scanning electron microscope photograph of a magnetic ion-exchange resin manufactured by using 10 mg/ml nanoscale magnetic iron oxide ($Fe_3O_4$) solution.

FIGS. 6 and 7 are the scanning electron microscope photographs of a magnetic ion-exchange resin manufactured by 5 mg/ml, 10 mg/ml nanoscale magnetic iron oxide ($Fe_3O_4$) solution. The present magnetic ion-exchange resin has spherical shape with uniform particle diameter distribution. The initial ion-exchange resin has spherical shape with average particle diameter of 144±23 μm, the magnetic ion-exchange resin manufactured from 5 mg/ml $Fe_3O_4$ magnetic nano-particles solution has spherical shape with average particle diameter of 176±14 nm, and the magnetic ion-exchange resin manufactured from 10 mg/ml $Fe_3O_4$ magnetic nano-particles solution has spherical shape with average particle diameter of 194±16 μm. It is shown that the particle diameters of magnetic ion-exchange resin increase with the amount of $Fe_3O_4$ magnetic nano-particles adsorbed into ion-exchange resin.

The saturation magnetization of magnetic ion-exchange resin manufactured from 10 mg/ml $Fe_3O_4$ magnetic nano-particles solution was determined to be 3.60±0.16 emu/g. Compared with the non-magnetic ion-exchange resin, the suspension of the magnetic ion-exchange resin is apt to be separated by using of Millitenyi Biotec's magnetic base MAFSiMAG™ Seperator. Capturing magnetic ion-exchange resin, manufactured from 10 mg/ml $Fe_3O_4$ magnetic nano-particles solution by the magnetic base only takes 4 seconds. Under weak magnetic condition, capturing the magnetic ion-exchange resin manufactured from initial 5 mg/ml $Fe_3O_4$ magnetic nano-particles solution by the magnetic base takes about 9 seconds. However, the times taken by the above magnetic ion-exchange resins are shorter than that taken by non-magnetic ion-exchange resins (average time of 42 seconds). Reason thereof is that non-magnetic ion-exchange resins settle to the bottom of test tube only by gravity, and part resin particles are attached to the inside of test tube. The advantages of the magnetic ion-exchange resin in this example are apt to be quickly collected and separated from the solution by using the magnetic field.

EXAMPLE 5

Separating Plasmid DNA by Using the Ion-Exchange Resin Manufactured in Example 4

10 mg of magnetic anion exchange resin manufactured from Example 4 is fully mixed with 1 ml of the cell crude extract prepared form Example 3 and 1 ml of the binding buffer (10 mM Tris-HCl, 1 M NaCl, 1 mM EDTA, pH=6.5) for 5 minutes. The magnetic nano-particles are separated from the solution by the magnetic base and removing the supernatant, sequentially washed three times with 2 ml of washing buffer (10 mM Tris-HCl and 1 mM EDTA, pH=8). The purified plasmid DNA solution is obtained after two times with 1 ml of desorption solution (1.5 M NaCl, 0.01 M Tris-HCl, 1 mM EDTA, pH=9.0). Table 3 shows $Abs_{260}/Abs_{280}$ ratio, protein concentration, RNA concentration and DNA concentration of the supernatant before purification (i.e., the supernatant of the cell crude extract), adsorbing residual solution, first washing supernatant, second washing supernatant, third washing supernatant, first desorption solution, second desorption solution.

The example confirms that the magnetic ion-exchange resin of the present invention can selectively adsorb DNA and thus render amounts of proteins and RNA in the desorption solutions very small. With the total amounts of DNA from first desorption solution and second desorption solution, the amount of selectively adsorbed plasmid DNA by per gram of magnetic ion-exchange resin is measured to 8.76 mg, higher than that in Example 3, which results from the smaller particle diameter of magnetic ion-exchange resin in this Example to allow the larger adsorption amount of DNA by per gram.

10, and then incubated in shaker incubator (170 rpm) at a temperature of 37° C. for 4-5 days. The medium is centrifuged at 13,000 rpm for 30 minutes at 37° C. And then ammonium sulfate at 90% saturation is used to obtain the precipitate from the supernatant. The precipitate is centrifugated at 13,000 rpm, re-dissolved in 0.1 mM of Tris(hydroxymethyl)aminomethane hydrochloride buffer solution (pH 7.0), and then dialyzed to obtain an enzyme solution containing 45 kDa xylanase which has pI value of 4.5.

The magnetic ion-exchange resin prepared from Example 2 (ion-exchange resin Lewatit® MonoPlus MP64, 10 mg/ml of magnetic nano-particles, the pH value is 12) is immersed in the above enzyme solution at 4° C. for 24 hours to form a mixture, wherein pH value of the mixture is 12 in order to allow enzyme to be immobilized to the magnetic ion exchange resin.

A substrate solution (per milliliter) is mixed with 50 mg of the magnetic ion-exchange resin immobilized with xylanase (0.255 U) to react at 50° C., wherein the substrate solution is 2.0% (w/v) xylan dissolved into 100 mM Tris-HCl buffer (pH 8.0). The substrate is xylan obtained from corn cobs after alkaline extraction with 15% NaOH to react at 90° C. for 90 minutes. The alkaline extract was neutralized with acetic acid to pH 5.0, and the xylan was obtained by three times its volume of 95% ethanol precipitation for 60 minutes.

Enzyme reaction is to convert substrate xylan into xylo-oligosaccharide (xylobiose, xylotriose and soluble xylo-oligosaccharide with degree of polymerization more than 4) in use of the magnetic ion-exchange resin immobilized with xylanase. After reaction for 24 hours, the conversion of xylan was approximately 74.4%, and the total fraction of xylobiose and xylotriose in the obtained product was approximately 24.6%. The magnetic ion-exchange resin of this Example can be applied for the preparation of immobilized enzyme as the catalyst of biochemical reactions.

Referring to Examples 1 to 6, the method of the present invention for preparing magnetic ion-exchange polymer micro spheres is simple. The magnetic nano-particles are not apt to leak out, because the magnetic nano-particles embedded in magnetic ion-exchange resin are mainly trapped in the

TABLE 3 the results of purification DNA from a magnetic anion exchange resin (manufactured from Example 4, 10 mg)

| Solution | $Abs_{260}/Abs_{280}$ | Protein concentration (µg/ml) | RNA concentration (µg/ml) | DNA amount (µg) |
|---|---|---|---|---|
| Supernatant of the cell crude extract | 2.1 ± 0.01 | 100.47 ± 4.89 | 468 | 626.03 ± 7.64 |
| Adsorbing residual solution | 1.97 ± 0.01 | 71.09 ± 0.81 | 413.6 | 486.47 ± 13.63 |
| $1^{st}$ washing supernatant | 1.88 ± 0.07 | 18.68 ± 0.7 | 60.8 | 55.73 ± 0.80 |
| $2^{nd}$ washing supernatant | 2.10 ± 0.6 | 3.95 ± 0.48 | 8.02 | 12.80 ± 6.61 |
| $3^{rd}$ washing supernatant | 1.98 ± 0.07 | 1.86 ± 0.48 | N/A | 5.07 ± 1.95 |
| $1^{st}$ desorption solution | 1.85 ± 0.03 | 0.70 ± 0.13 | 1.08 | 55.93 ± 4.76 |
| $2^{nd}$ desorption solution | 1.85 ± 0.01 | 1.09 ± 0.16 | 0.8 | 31.67 ± 4.88 |

EXAMPLE 6

Immobilizing Enzyme by Using the Magnetic Ion-Exchange Resin Manufactured in Example 2

*Bacillus halodurans* are inoculated into Emerson medium (0.55% yeast extract, 0.5% digested protein, 0.02% magnesium sulfate, and 0.1% dipotassium hydrogen phosphate, pH=10) containing 2% of corn cobs, and the pH is adjusted to network structure of polymer chains. Further, it is confirmed that the present magnetic ion-exchange resin can be applied to separate DNA and immobilize enzyme.

What is claimed is:

1. A method for preparing magnetic ion-exchange polymer microspheres comprises the steps of:
   (a) preparing ion-exchange polymer microspheres having a charged functional group, and immersing the ion-exchange polymer microspheres having a charged functional group into a solution in order to swell the ion-exchange polymer microspheres, and the ion-exchange polymer microspheres having a charged functional group are made of polystyrene, or a copolymer including styrene and at least one monomer, wherein the polystyrene or the copolymer forms a network structure of polymer chains by adding a cross-linking agent, and the solution allows the network structure of polymer chains to swell and expand;

(b) adding a colloid solution containing magnetic nano-particles into the solution to form a mixture and adjusting the pH value of the mixture to 8-12 in order to allow the magnetic nano-particles to enter into the network structure of polymer chains, wherein the amount of magnetic nano-particles entrapped within the network structure of polymer chains is changed with the pH value; and (c) separating the ion-exchange polymer microspheres from the solution, wherein the ion-exchange polymer microspheres are non-porous, and the ion-exchange polymer microspheres shrink after removing the solution to allow the network structure of polymer chains to become compact, then the magnetic nano-particles are entrapped within the network structure of polymer chains.

2. The method as claimed in claim 1, wherein the ion-exchange polymer microspheres are made of polystyrene, or a copolymer including styrene as monomer having a positively charged functional group or a negatively charged functional group.

3. The method as claimed in claim 2, wherein the monomer is a vinyl monomer with at least one functional group.

4. The method as claimed in claim 1, wherein the cross-linking agent is divinylbenzene.

5. The method as claimed in claim 1, wherein particle diameter of the ion-exchange polymer microspheres is 0.1 μm-1 mm.

6. The method as claimed in claim 1, wherein a polarity parameter value of the Hansen solubility parameter of the solution is between 2 $(cal/cm^3)^{1/2}$ and 12 $(cal/cm^3)^{1/2}$, and a hydrogen bonding parameter value is between 2 $(cal/cm^3)^{1/2}$ and 8 $(cal/cm^3)^{1/2}$.

7. The method as claimed in claim 6, wherein the polarity parameter value of the Hansen solubility parameter of the solution is between 5 $(cal/cm^3)^{1/2}$ and 9 $(cal/cm^3)^{1/2}$, and the hydrogen bonding parameter value is between 3 $(cal/cm^3)^{1/2}$ and 6 $(cal/cm^3)^{1/2}$.

8. The method as claimed in claim 1, wherein the solution includes a solvent, and the solvent is a dipolar aprotic solvent.

9. The method as claimed in claim 1, wherein a material of the magnetic nano-particles is selected from the group consisting of iron oxide, ferromagnetic oxide, ferromagnetic nickel, ferromagnetic cobalt, iron-cobalt-nickel alloy, iron carbide (FeC), and iron platinum (FePt) alloy.

10. The method as claimed in claim 9, wherein the iron oxide is selected from the group consisting of $Fe_3O_4$ and $Fe_2O_3$.

11. The method as claimed in claim 9, wherein the ferromagnetic oxide is selected from the group consisting of $MnZnFe_2O_4$ and $NiZnFe_2O_4$.

12. The method as claimed in claim 1, wherein the pH value in step (b) is 10-12.

13. The method as claimed in claim 1, further comprising washing the ion-exchange polymer microspheres with methanol or distilled water after the step (c).

\* \* \* \* \*